US011815431B2

(12) United States Patent
Shkunov et al.

(10) Patent No.: US 11,815,431 B2
(45) Date of Patent: Nov. 14, 2023

(54) ELECTRICAL GAS DETECTOR COMPRISING AN ARENE-FUNCTIONALIZED NANOWIRE

(71) Applicant: UNIVERSITY OF SURREY, Surrey (GB)

(72) Inventors: Maxim Shkunov, Guildford (GB); Marios Constantinou, Surrey (GB); Angela Danil De Namor, Surrey (GB)

(73) Assignee: University of Surrey

( * ) Notice: Subject to any disclaimer, the term of this patent is extended or adjusted under 35 U.S.C. 154(b) by 972 days.

(21) Appl. No.: 16/464,624

(22) PCT Filed: Nov. 27, 2017

(86) PCT No.: PCT/GB2017/053564
§ 371 (c)(1),
(2) Date: May 28, 2019

(87) PCT Pub. No.: WO2018/100346
PCT Pub. Date: Jun. 7, 2018

(65) Prior Publication Data
US 2020/0057019 A1 Feb. 20, 2020

(30) Foreign Application Priority Data
Nov. 29, 2016 (GB) ...................... 1620234

(51) Int. Cl.
*G01N 27/414* (2006.01)
*G01N 33/00* (2006.01)

(52) U.S. Cl.
CPC ..... *G01N 27/4141* (2013.01); *G01N 27/4146* (2013.01); *G01N 33/0047* (2013.01)

(58) Field of Classification Search
CPC ... G01N 27/4141; G01N 27/414–4168; G01N 27/4167; G01N 27/4146; G01N 33/0047; G01N 33/0057; H01L 29/2924; H01L 29/13073; H01L 29/772–8128
See application file for complete search history.

(56) References Cited

U.S. PATENT DOCUMENTS

2008/0116490 A1 5/2008 Stewart et al.
2010/0198521 A1* 8/2010 Haick ................ G01N 27/4146
706/14
2013/0059758 A1 3/2013 Haick et al.
(Continued)

OTHER PUBLICATIONS

Paska et al., acsnano, 2011, 5620-5626 (Year: 2011).*
(Continued)

*Primary Examiner* — Gurpreet Kaur
(74) *Attorney, Agent, or Firm* — Ryan Dean; Umberg Zipser LLP

(57) ABSTRACT

The present invention provides a gas detector for detecting a volatile organic compound (VOC) gas. The gas detector comprises at least one transducer comprising at least one nanowire comprising an arene compound to capture a VOC gas. An electronic characteristic of the transducer changes when a VOC gas is captured by the arene compound. The present invention also provides a mobile device; a nanowire; a nanowire matrix; a transducer; a use of a gas detector; a method of detecting a VOC gas; and a method of manufacturing a gas detector.

16 Claims, 8 Drawing Sheets

(56) References Cited

U.S. PATENT DOCUMENTS

2016/0011135 A1   1/2016  Wang et al.
2016/0231267 A1   8/2016  Swager et al.

OTHER PUBLICATIONS

Anatoliy N Sokolov et al: "Induced Sensitivity and Selectivity in Thin-Film Transistor Sensors via Calixarene Layers", Advanced Materials, Jun. 4, 2010, vol. 22, No. 21, (Jun. 4, 2010), pp. 2349-2353, Germany.
European Patent Office, International Search Report and Written Opinion, dated Feb. 13, 2018.
United Kingdom Intellectual Property Office, Search Report, dated Jun. 2, 2017.

* cited by examiner

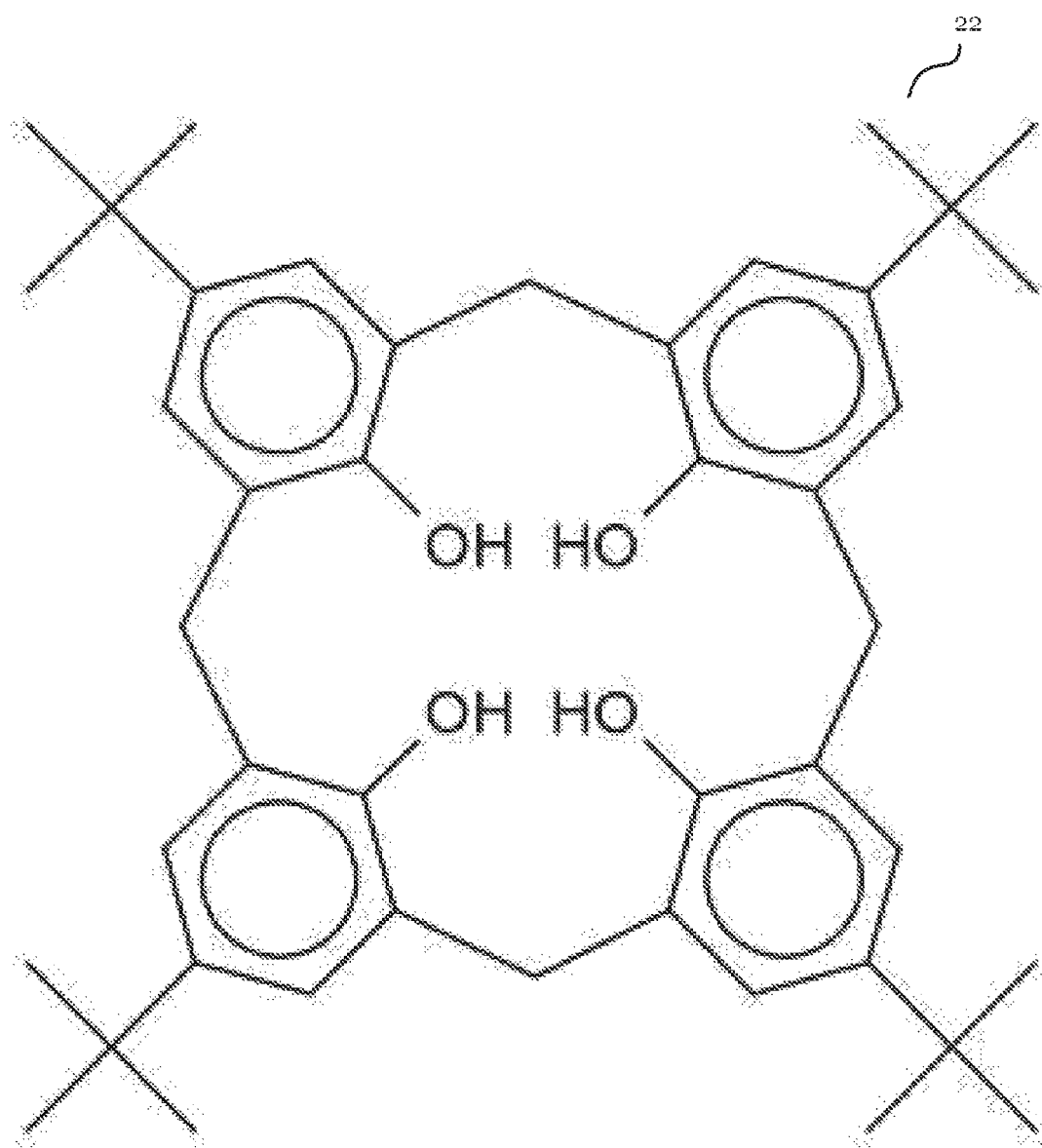

ELECTRICAL GAS DETECTOR COMPRISING AN ARENE-FUNCTIONALIZED NANOWIRE

The present invention relates to gas detectors, and especially to volatile organic compound (VOC) gas detectors. More specifically, the present invention relates to benzene, toluene, ethylbenzene and xylene (BTEX) gas detectors, and to methods of detecting VOCs.

Sensing hazardous aromatic volatile organic compounds (VOCs) is of utmost importance to reduce health risk and ensure public safety. The chronic exposure to VOCs, such as benzene, toluene, ethylbenzene and xylene (BTEX) pollutants, causes cancer (e.g. acute nonlymphocytic leukemia (ANLL), acute myeloid leukemia (AML) and non-Hodgkin's lymphoma (NHL)) and damages the immune system (e.g. oxidative stress, insulin resistance (IR) and DNA methylation changes), raising the demand for the development of reliable, high-performance and highly selective gas sensors. Sensing benzene vapours has become a challenging task mainly because of benzene's neutral polarity and size, as it is one of the smaller molecules of the BTEX family. In the UK, around 640 thousand tons of benzene are used, mainly in the manufacture of other chemicals, such as plastics, foams, dyes, detergents, solvents, drugs and insecticides. Based on the massive use of benzene, exposure tolerance limits are very strict and the rapid detection at low concentrations is tremendously important.

Alternative sensing technologies have been attractive for sensing BTEX VOC gases at low concentrations, but the detection selectivity is still a challenge. In addition, many sensors are expensive and the detection of BTEX gases in a variety of environments (such as those with high humidity) limits their affordability and usability. Detecting benzene and differentiating from other pollutants of the BTEX family is still a challenge.

Aspects of the present invention aim to address one or more drawbacks inherent in prior art methods and apparatus for detecting BTEX gases, particularly benzene.

According to a first aspect of the present invention, there is provided a gas detector for detecting a volatile organic compound (VOC) gas, the detector comprising at least one transducer comprising at least one nanowire comprising an arene compound to capture a VOC gas, wherein an electronic characteristic of the transducer changes when a VOC gas is captured by the arene compound.

Advantageously, the claimed gas detector provides a means to easily and cheaply detect the presence of VOC gases. Moreover, the claimed gas detector provides a means to differentiate between different VOC gases (and preferably BTEX gases) with high specificity, and determine their relative concentration.

Preferably, therefore, the VOC gas is a BTEX gas. Even more preferably, the BTEX gas is one of benzene, toluene, ethylbenzene and xylene. Most preferably, the BTEX gas is benzene.

Preferably, the arene compound comprises a calixarene compound. Suitably, the arene compound may comprise an arene compound selected from a group consisting of: calix[4]arene; resorc[4]arene; pyrogallol[4]arene; and calix[5]arene. Most preferably, the arene compound comprises a calix[4]arene compound. More preferably, the arene compound comprises a calix[4]resorcinarene (also known as resorcinarene or resorcarene) compound.

Preferably, the at least one nanowire comprises an undoped semiconductive nanomaterial having stable surface chemistry. Even more preferably, the at least one nanowire comprises a silicon nanowire. Alternatively, the at least one nanowire comprises a single dimensional undoped or lightly doped nanomaterial coated in a thin dielectric layer.

Preferably, the transducer comprises a field effect transistor (FET) comprising a source electrode, a gate electrode, and a drain electrode, wherein the at least one nanowire is coupled between the source electrode and the drain electrode. Even more preferably, the gas detector comprises a power source for driving a gate voltage $V_G$ and a source voltage $V_{SD}$.

Preferably, the gas detector comprises a controller configured to measure the electronic characteristic of the transducer and determine whether a VOC gas is captured. Even more preferably, the controller is configured to measure the threshold gate voltage $V_{TH}$ necessary to drive the FET, calculate the change in Val relative to a predetermined $V_{TH}$, and compare the change in $V_{TH}$ with a threshold, wherein, a VOC gas is determined to be captured if the change in $V_{TH}$ is greater than a threshold. The predetermined $V_{TH}$ is the $V_{TH}$ measured in pure air.

Preferably, the controller is configured to measure $V_{TH}$ by:
increasing $V_G$ in increments and measuring the current $I_D$ at the drain electrode for each increment of $V_G$ to plot an $I_D/V_G$ curve;
identifying the linear region of the $I_D/V_G$ curve; and
extrapolating the linear region to the intersect with the $I_D=0$ axis such that the threshold $V_G$ at this intersect is determined.

Alternatively, the controller is configured to measure $V_{TH}$ by:
increasing $V_G$ in increments and measuring the current $I_D$ at the drain electrode for each increment of $V_G$ to plot an $I_D/V_G$ curve; and
measuring $V_{TH}$ by determining the gate voltage value corresponding to the maximum value of the second derivative of the $I_D/V_G$ curve.

Alternatively, the transducer may comprise a resistor, and a controller is preferably configured to measure the voltage and current across the ends of the resistor to determine its resistance. Preferably, the controller is configured to calculate the change in the resistance of the resistor relative to a predetermined resistance, and compare the change in resistance with a threshold.

Preferably, the gas detector comprises a storage device for storing a lookup table for comparing the change in $V_{TH}$, VOC gas type and the concentration of the VOC gas. Even more preferably, the controller is configured to determine the VOC gas type and the concentration of VOC gas using the lookup table and the measured change in $V_{TH}$. Each lookup table is associated with a particular arene compound.

Preferably, the gas detector comprises a plurality of transducers arranged in a matrix, each comprising a different arene compound.

Preferably, the gas detector comprises at least one of a display device and an audio device, and the controller is configured to alert a user to the presence of a VOC gas if the electronic characteristic changes more than a threshold amount.

Preferably, the gas detector comprises an interface for transmitting an indication of the presence of a VOC gas to an external computing device. Even more preferably, an indication of the concentration of the VOC gas is transmitted to the external computing device if the concentration of the VOC gas exceeds a threshold.

According to a second aspect of the present invention, there is provided a nanowire comprising an arene compound arranged to capture a volatile organic compound (VOC) gas.

Preferably, therefore, the VOC gas is a BTEX gas. Even more preferably, the BTEX gas is one of benzene, toluene, ethylbenzene and xylene. Most preferably, the BTEX gas is benzene.

Preferably, the arene compound comprises a calixarene compound. Suitably, the arene compound may comprise an arene selected from a group consisting of: calix[4]arene; resorc[4]arene; pyrogallol[4]arene; and calix[5]arene. Most preferably, the arene compound comprises a calix[4]arene compound. More preferably, the arene compound comprises a calix[4]resorcinarene (also known as resorcinarene or resorcarene) compound.

Preferably, the at least one nanowire comprises an undoped semiconductive nanomaterial having stable surface chemistry. Even more preferably, the at least one nanowire comprises a silicon nanowire. Alternatively, the at least one nanowire comprises a single dimensional undoped or lightly doped nanomaterial coated in a thin dielectric layer.

According to a third aspect of the present invention, there is provided a nanowire matrix comprising a plurality of nanowires according to the second aspect, wherein at least two or more nanowires comprise an arene compound arranged to capture a different VOC gas.

According to a fourth aspect of the present invention, there is provided a transducer comprising one or more nanowire according to the second aspect, or one or more nanowire matrix according to the third aspect.

Preferably, the transducer is a transistor or a resistor. Preferably, the transducer is a field effect transistor (FET).

According to a fifth aspect of the present invention, there is provided use of the nanowire according to the second aspect, the nanowire matrix according to the third aspect, or the transducer of the fourth aspect, for detecting a VOC gas.

According to a sixth aspect of the present invention, there is provided a mobile device comprising the gas detector according to the first aspect, the nanowire according to the second or third aspect, or the transducer according to the fourth aspect.

Preferably, the mobile device comprises a smart phone or a tablet.

According to a seventh aspect of the present invention, there is provided a method of detecting a VOC gas using a gas detector comprising at least one transducer, comprising:
applying a voltage across ends of at least one nanowire comprising an arene compound to capture a VOC gas wherein an electronic characteristic of the transducer changes when the VOC gas is captured by the arene compound; and
measuring the electronic characteristic.

Preferably, the VOC gas is a BTEX gas. Even more preferably, the BTEX gas is one of benzene, toluene, ethylbenzene and xylene. Most preferably, the BTEX gas is benzene.

Preferably, the arene compound comprises a calixarene compound. Suitably, the arene compound may comprise an arene selected from a group consisting of: calix[4]arene; resorc[4]arene; pyrogallol[4]arene; and calix[5]arene. Most preferably, the arene compound comprises a calix[4]arene compound. More preferably, the arene compound comprises a calix[4]resorcinarene (also known as resorcinarene or resorcarene) compound.

Preferably, the method comprises determining whether a VOC gas is captured by the arene compound. Even more preferably, the transducer comprises a field effect transistor FET, and measuring the electronic characteristic preferably comprises:
measuring the threshold gate voltage Val necessary to drive the FET at a predetermined source voltage $V_{SD}$;
calculating the change in $V_{TH}$ relative to a predetermined $V_{TH}$, and comparing the change in $V_{TH}$ with a threshold, wherein, a VOC gas is determined to be captured if the change in $V_{TH}$ is greater than a threshold.

Preferably, measuring $V_{TH}$ comprises:
increasing the gate voltage $V_G$ in increments and measuring the current $I_D$ at the drain electrode of the FET for each increment of $V_G$ to plot an $I_D/V_G$ curve;
identifying the linear region of the $I_D/V_G$ curve; and
extrapolating the linear region to the intersect with the $I_D=0$ axis such that the threshold $V_G$ at this intersect is determined.

Alternatively, measuring $V_{TH}$ comprises:
increasing $V_G$ in increments and measuring the current $I_D$ at the drain electrode for each increment of $V_G$ to plot an $I_D/V_G$ curve; and
measuring $V_{TH}$ by determining the gate voltage value corresponding to the maximum value of the second derivative of the $I_d/V_G$ curve.

Alternatively, the transducer comprises a resistor, and the measuring the electronic characteristic preferably comprises measuring the voltage $V_R$ and current $I_R$ across the ends of the resistor to determine the resistance of the resistor. Even more preferably, the method comprises calculating the change in the resistance of the resistor relative to a predetermined resistance, and comparing the change in resistance with a threshold.

Preferably, the method comprises dissolving calix in an organic solvent and applying the resulting calixarene compound to the at least one nanowire. Even more preferably, the method comprises dissolving the calix in toluene or chloroform. Even more preferably, applying the calixarene compound to the at least one nanowire comprises drop-casting the calixarene compound. Alternatively, applying the calixarene compound to the at least one nanowire comprises spin-coating the calixarene compound. Even more preferably, the calixarene compound is spin-coated, for example at about 500-3000 rpm for at least 5 seconds, or preferably about 1500 rpm for about 10 seconds.

Preferably, the method comprises:
dissolving about 6 mg of calix in about 3 ml of toluene or chloroform; and
baking the transducer at less than 100 degrees Celsius to evaporate the residues of the dissolving solvent.

Even more preferably, the method comprises baking the transducer at 90 degrees Celsius.

Preferably, applying the calixarene compound to the at least one nanowire comprises drop-casting the calixarene compound. Alternatively, applying the calixarene compound to the at least one nanowire comprises spin-coating the calixarene compound. Even more preferably, the calixarene compound is spin-coated at about 1500 rpm for about 10 seconds.

Preferably, the method comprises alerting a user to the presence of a VOC gas if the electronic characteristic changes more than a threshold amount.

Preferably, the method comprises transmitting an indication of the presence of a VOC gas to an external computing device.

According to an eighth aspect of the present invention there is provided a method of manufacturing a gas detector, comprising:

coupling at least one nanowire between ends of a transducer; and applying an arene compound to the at least one nanowire. Preferably, the method comprises:

dissolving calix in an organic solvent to produce a calixarene;

applying the calixarene compound to the at least one nanowire; and baking the transducer at less than 100 degrees Celsius to evaporate the residues of the dissolving solvent.

Preferably, the method comprises baking the transducer at 90 degrees Celsius.

Preferably, the method comprises dissolving calix in toluene or chloroform. Even more preferably, the method comprises dissolving about 6 mg of calix in about 3 ml of toluene or chloroform.

Even more preferably, applying the calixarene compound to the at least one nanowire comprises drop-casting the calixarene compound. Alternatively, applying the calixarene compound to the at least one nanowire comprises spin-coating the calixarene compound. Even more preferably, the calixarene compound is spin-coated, for example at about 500-3000 rpm for at least 5 seconds, or preferably about 1500 rpm for about 10 seconds.

Preferably, the arene compound comprises a calixarene compound. Suitably, the arene compound may comprise an arene selected from a group consisting of: calix[4]arene; resorc[4]arene; pyrogallol[4]arene; and calix[5]arene. Most preferably, the arene compound comprises a calix[4]arene compound. More preferably, the arene compound comprises a calix[4]resorcinarene (also known as resorcinarene or resorcarene) compound.

All features described herein (including any accompanying claims, abstract and drawings), and/or all of the steps of any method or process so disclosed, may be combined with any of the above aspects in any combination, except combinations where at least some of such features and/or steps are mutually exclusive.

BRIEF DESCRIPTION OF THE FIGURES

Embodiments of the present invention will now be described, by way of example only, with reference to the accompanying drawings, in which:

FIG. 5 is a plan view of a calix[4]arene derivative; and

In the drawings, like reference numerals refer to like features throughout.

With reference to FIG. 1, a transducer 10 having at least one chemical characteristic that changes in the presence of BTEX gas molecules will be described. The transducer 10 is for use in a gas detector 100, which will be described in more detail with reference to FIG. 2.

Figure 1:
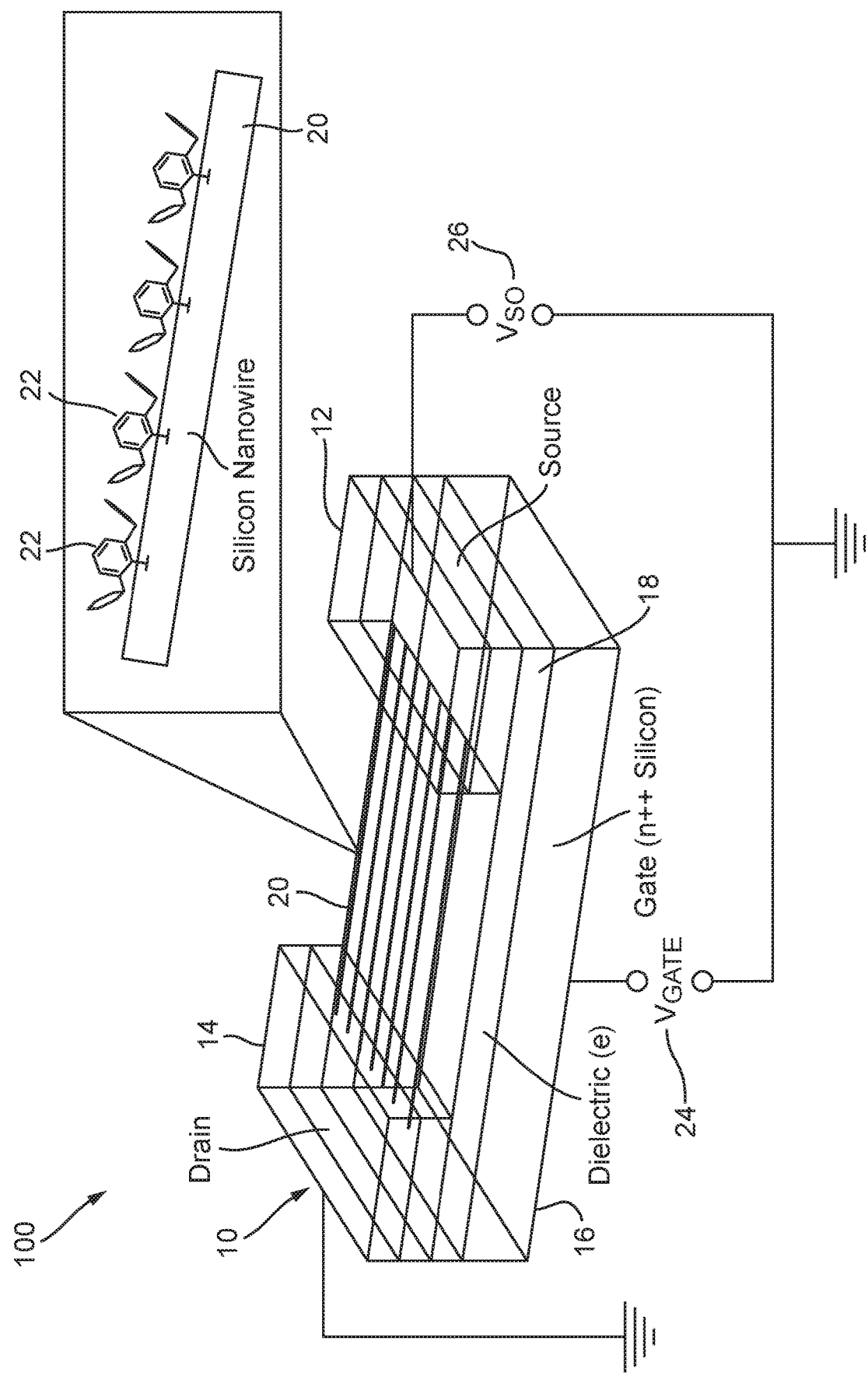
FIG. 1 is a perspective view of part of one embodiment of a gas detector according to the present invention.

In the embodiment shown in FIG. 1, the transducer 10 is a field effect transistor (FET). A FET is an electronic switching device that uses an electric field to control the shape and hence electrical conductivity of a channel between a source electrode 12 and a drain electrode 14. The electric field is generated by applying a gate voltage $V_G$ 24 to a gate electrode 16 of the FET. When $V_G$ 24 reaches a threshold gate voltage $V_{TH}$, current is able to flow from the source electrode 12 to the drain electrode 14 when a potential difference $V_{SD}$ 26 is applied across them. $V_{SD}$ 26 according to a preferred embodiment is a low voltage bias, for example between 1 and 2 Volts. $V_{SD}$ is significantly smaller than $V_G$, but its value is not critical to the operation of the inventive concept.

The FET shown in FIG. 1 is an p-channel silicon device, with the gate electrode 16 being made of a highly doped $n^{++}$ crystalline silicon. It would be appreciated by the skilled person that n-channel devices may also be used.

The gate electrode 16 is disposed on one side of a dielectric material 18. The dielectric material 18 is, for example, silicon dioxide. A source electrode 12 and drain electrode 14 are disposed on the opposite side of the dielectric material 18, and spaced apart from each other.

A plurality of nanowires 20 extend in a channel between the source electrode 12 and the drain electrode 14. In a preferred embodiment, the nanowires 20 are silicon nanowires with a native oxide shell layer. $SiO_2$ is inert and does not interact with analyte molecules. However, in practice the nanowires 20 could be made of any semiconducting one dimensional (1D) intrinsic (un-doped) nanomaterial provided it has a very stable surface chemistry. The surface chemistry can be effectively made stable through coating the nanowires 20 in a very thin dielectric layer with inert characteristics. For example, the nanowires 20 can be coated in ultrathin alumina ($Al_2O_3$). Such dielectric layer needs to be very thin, approximately 10 nm, with thickness being less than Debye screening length in alumina $Al_2O_3$ of 31 nm. Atomic layer deposition (ALD) may be used to deposit the dielectric layer.

Other inorganic nanowire materials, such as Ge, ZnO, InAs, etc., have their own surface chemistry that might result in some sensing events, and these are not specific for the target BTEX gas molecules. Carbon nanotubes do not provide a good alternative since their surface might be susceptible to various molecular interactions, meaning a loss of selectivity. Unprotected semiconducting single wall carbon nanotubes (s-SWCNT) are not very useful for direct receptor attachment on nanowires since any covalent bonds will disrupt pi-pi bonding on the SWCNT, resulting in a loss of electrical performance.

The length of the nanowires 20 is sufficient to bridge the transducer's 10 source and drain electrodes (typically greater than 5 microns, but preferably greater than 10 microns), and have relatively small diameters (30-60 nm) so that changes in the local surface potential can efficiently affect charge carriers in the nanowires 20.

FETs are particularly suitable to the present application due to their high sensitivity and the degree to which they can be controlled. Moreover, they allow for a number of variables to be measured, such as subthreshold slope and channel resistance, so that extended analysis of the atmosphere can be performed.

The nanowires 20 are coated in a receptor material 22. Specifically, the receptor material 22 is an arene compound such as a calix[4]arene derivative. More specifically, the arene compound is one which adopts a 'cone' conformation and therefore contains a hydrophobic cavity. As the number of phenyl units increase the 'cone' conformation is lost and loses its ability to receive BTEX gas molecules. Therefore, the arene compound is one of calix[4]arene, resorc[4]arene, pyrogallol[4]arene and calix[5]arene. The nanowires 20 may not be completely coated, and instead the receptor material 22 may be affixed to a portion of their surface area.

The receptor material 22 traps BTEX gas molecules that are present in the surrounding atmosphere. These gas molecules increase the electrical resistance of the nanowires 20 and therefore increase the necessary threshold voltage $V_{TH}$ for turning on the FET. The greater the change in measured $V_{TH}$ from $V_{TH}$ in pure air, the greater the concentration of BTEX gas molecules present.

As shown in FIG. 5, the molecular structure of the receptor material 22 is comprised of: functionalised calix, a spacer group, and an anchor group to covalently bind the receptor material 22 to the surface of the nanowires 20. Each compound of the calix[4]arene family of molecules (i.e. calix[4]arene and calix[4]resorcinarene (also known as resorcinarene or resorcarene) compound) is selective to a particular analyte, such as benzene, toluene, ethylbenzene and xylene, through functionalisation of the top rim of the calix. The receptor material's 22 cavities provide the binding sites for the BTEX gases, forming a guest-host assembly. Calix[4]arene derivatives selectively absorb the desired BTEX gas guest molecules and bind them through non-covalent interactions such as Van der Waals interactions. Calix[4]arene derivatives are particularly well suited to applications for detecting BTEX gas molecules due to size of their binding points.

Advantageously, the binding between calix[4]arene derivatives and the BTEX gas molecules is reversible. In other words, the BTEX gas molecules can be released and subsequently new BTEX gas molecules can be captured. The recovery time of calix[4]arene derivatives is of the order of seconds. The reversibility is obtained either by heating the nanowires 20 to low temperatures (for example 60 Celsius degrees, which is suitable for plastic electronics) for 30 seconds or by applying a low voltage bias across the source electrode 12 and drain electrode 14.

In addition, the hydrophobic surface nature of calix[4] arene derivatives provide a weak interaction with —OH groups, hence the water vapour effect which limits the adsorption of non-polar volatile organic compounds (VOCs) is minimised to the point where it is effectively negligible. This indicates the high suitability for the use of calix[4]arene derivatives as the receptor material 22 in highly humid environments.

In other words, arene compounds, especially calix[4] arene derivatives, are particularly well suited for use in electronic gas detectors 100.

Figure 2:
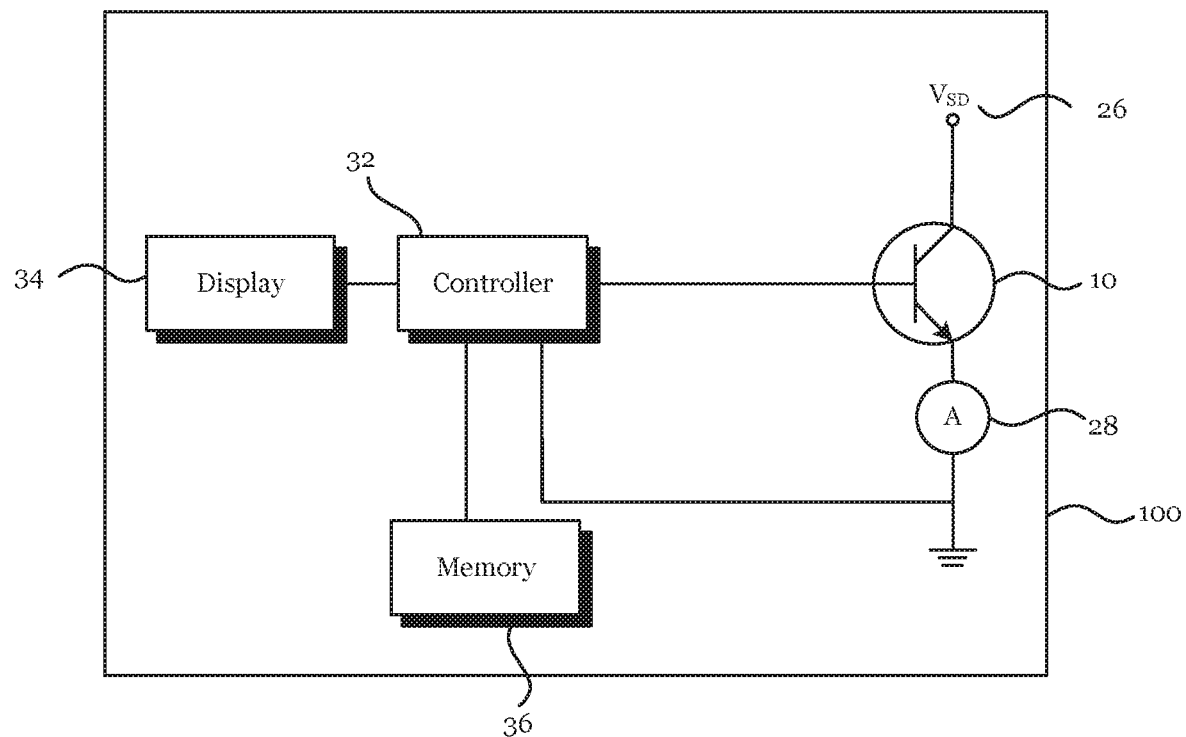
FIG. 2 is a system view of a gas detector according to the present invention.

The gas detector 100 will now be described in more detail with reference to FIG. 2. The transducer 10 is a relatively low power and compact device, and therefore can easily be mounted in a mobile device, such as a smart phone. Alternatively, the gas detector 100 may be ruggedized and integrated into an environment, such as a recycling centre or landfill.

The gas detector 100 comprises a power supply (not shown) such as a battery cell for driving $V_{SD}$ 26 and $V_G$ 24, as well as powering other electronic components of the gas detector 100 such as a display 34 and a controller 32. Alternatively, the power supply may be external to the gas detector 100. The gas detector 100 may be mains powered.

The controller 32, for example a microprocessor, is arranged to control $V_G$ 24 to scan between a range of values in increments. For example, the controller 32 is configured to ramp up $V_G$ 24 in 0.1 Volt increments from −40 Volts to 0 Volts.

An ammeter 28 is coupled between the controller 32 and the transducer 10. In practice, the ammeter 28 may be part of the controller 32. The ammeter 28 measures the current at the end of the transducer 28. More specifically, according to the preferred embodiment, the ammeter 28 measures the current at the drain electrode 14.

The controller 32 is configured to measure a change in an electronic characteristic of the transducer 10. In a preferred embodiment, the controller 32 measures the current $I_D$ across a FET, and plots it against the gate voltage $V_G$ in order to determine the threshold gate voltage $V_{TH}$ Val for an identical FET having the same source voltage $V_{SD}$ applied changes according to whether or not BTEX gas molecules are present in the surrounding atmosphere. In other words, in pure air a FET will have one threshold voltage, and in air containing BTEX gas molecules the FET will have a different threshold voltage. The shift, or change, in $V_{TH}$ is proportional to the chemical concentration of the BTEX target molecule.

The core aspect of the present invention lies in the receptor material 22 being an arene compound disposed on the nanowires 20, binding with BTEX gas molecules to change an electronic characteristic of a transducer 10 to which the nanowires 20 are coupled. Therefore, while a FET has been described herein, the nanowires 20 could be coupled to any transducer 10 whose electronic characteristics can be measured.

Therefore, in alternative embodiments, the transducer 10 is a resistor. The nanowires 20 are coupled between distal ends of the resistor and coated in the receptor material 22, such as a calix[4]arene derivative. Here, the power supply drives a voltage $V_R$ across the transducer 10. The controller 32 uses the ammeter 28 to measure the current $I_R$ across the resistor to determine the resistance of the resistor according to the equation $R=V_R/I_R$. The coated nanowires 20 will change the resistance of the resistor when BTEX gas molecules are received by the receptor material 22. The controller 32 compares the measured resistance of the resistor with the resistance of the resistor measured in pure air in order to determine the change in the resistance. The change in resistance is compared with a threshold value in order to determine whether BTEX gas molecules are present and their relative concentrations. The resistor will have one resistance in pure air and a different resistance in air in which BTEX gas molecules are present.

The transducer 10 may alternatively be any other device whose electronic characteristics can be changed by coating nanowires 20 in a receptor material 22, specifically an arene compound, and placing the transducer 10 in the presence of BTEX gas molecules.

The gas detector 100 may comprise a plurality of transducers 10, such as the FET described with reference to FIG. 1, each optimised to detect different types of BTEX gases. The transducers 10 may be arranged in a matrix. Each transducer 10 in the matrix may have different calix[4]arene derivatives attached to its nanowires 20. Such a multi-elemental sensing platform provides instantaneous mapping of the different chemicals, or molecules, in the surrounding atmosphere.

The gas detector 100 further comprises a display 34 coupled to the controller 32. When a high concentration of BTEX gas molecules is present, for example when the change in the electronic characteristic exceeds a threshold, the controller 32 is configured to control the display 34 to show a warning message to the user. As BTEX gas molecules are so dangerous to humans, a "high" concentration may be quite a low concentration when compared with other molecules such as water vapour. For example, the threshold may be set such that the alert is triggered if the concentration of a particular BTEX gas molecule exceeds 0.5 ppm. In other embodiments, the threshold for triggering the alert is 5 ppm. The threshold is set according to the implementation. For example, it is recommended that people should not be exposed to an 8 hour time weighted average (TWA) greater than 1.0 ppm of benzene. This is equivalent to a threshold of 3.25 mg per metre cubed of benzene.

Alternatively, the controller 32 may simply control the display 34 to flash when the concentration of BTEX gas molecules exceeds a threshold. In further embodiments, the gas detector 400 includes a speaker instead of, or in addition to, the display 34 for warning the user of a high concentration of BTEX gas molecules being present.

The gas detector 100 comprises a memory 36 coupled to the controller 32. The memory includes programming instructions that, when executed, cause the controller 32 to determine whether BTEX gas molecules are present in the surrounding atmosphere. Moreover, the memory 36 includes a lookup table. The memory 36 is, for example, a solid state hard drive or other well-known storage medium. The memory 36 may alternatively be a component of the controller 32. In some embodiments, the control instructions are stored on a first memory and the lookup table is stored on a second memory.

The lookup table includes a list of change in threshold voltages $V_{TH}$, type of BTEX gas molecules and concentration of the type of gas molecules. The lookup table for each arene compound used is different, and therefore the memory 36 may store a plurality of lookup tables when a matrix of transducers 10 are present for chemical mapping. Therefore, for a known change in $V_{TH}$, the type of BTEX gas molecule present and its concentration can be predicted. This prediction is improved where there is no overlap between change in $V_{TH}$ for different BTEX gas molecules. For example, a very small change in $V_{TH}$ is unlikely to be a result of benzene molecules being present when a particular calix[4] arene derivative is used, as these molecules are known to have a strong impact on the resistance of nanowires 20 having that particular calix[4]arene derivative disposed thereon. Meanwhile, other calix[4]arene derivatives behave differently to the presence of benzene, and are more sensitive to toluene being present, for example.

In some cases, it is not necessary to differentiate between different BTEX gas molecules. In other words, any change in $V_{TH}$ is enough to trigger an alert.

In alternative embodiments, the gas detector 100 is configured to communicate measurements, or the indication of whether or not BTEX gas molecules are present in the atmosphere, via a wired or wireless interface to a terminal station. This prevents a user from having to enter a potentially dangerous environment in order to determine the concentration of, and/or type of, BTEX gas molecules present.

Figure 3:
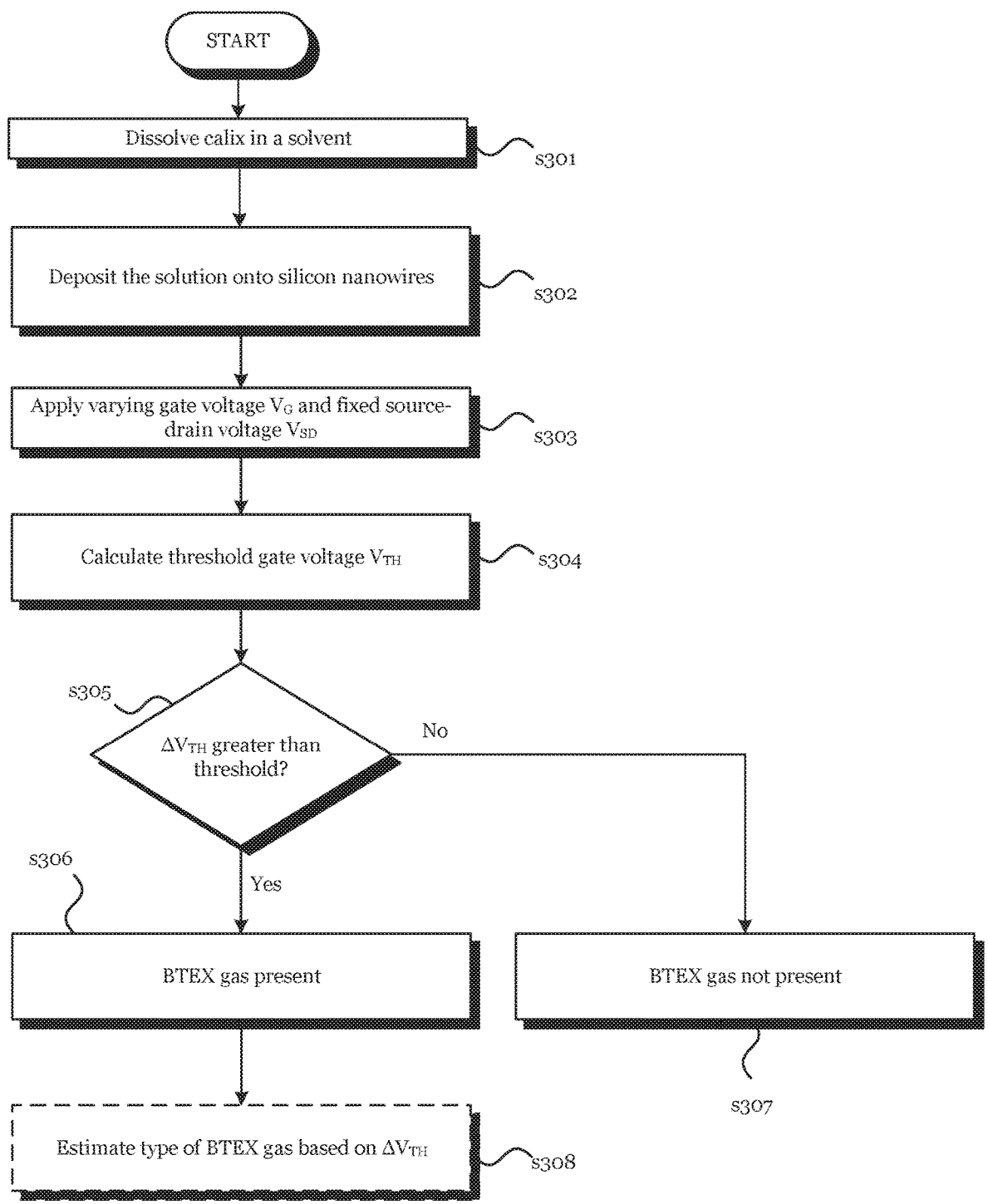
FIG. 3 is a flowchart showing a method of detecting gas according to an embodiment of the present invention.

Referring to FIG. 3, a method of detecting BTEX gas using a FET as a transducer 10 will now be described. In a first step S301, calix is dissolved in a solvent to produce a calixarene compound receptor material 22. According to a preferred embodiment, the solvent is toluene or chloroform. In the preferred embodiment, about 6 mg of calix is dissolved in about 3 ml of toluene or chloroform to produce a calix[4]arene derivative. However, this is not intended to be limiting, and various concentrations of calix may be mixed in different organic solvents to produce different calix[4] arene derivatives.

In step S302, the receptor material 22 is deposited onto the nanowires 20 extending between the source electrode 12 and the drain electrode 14 of the FET. According to a preferred embodiment, the receptor material 22 is spin-coated onto the nanowires 20. The spin-coating occurs at 1500 rpm for 10 seconds. The receptor material 22 is then dried (baked) at a temperature less than 100 degrees Celsius. Optimally, the receptor material 22 is baked at 90 degrees Celsius. These variables do not affect the functioning of the gas sensor 100. According to other embodiments, the receptor material 22 is drop-casted onto the nanowires 20.

Once the receptor material 22 has dried, the gas detector 100 can be operated to detect BTEX gas molecules. In step S303, the controller 32 applies a gate voltage $V_G$ 24 to the gate electrode 16 of the FET. $V_G$ is scanned, or ramped, between about 0 V and −40 V in increments. Each increment is about 0.1 V. The smaller the increment, the higher the accuracy of performed measurements. While $V_G$ is being applied, a constant source voltage $V_{SD}$ is applied across the source electrode 12 and the drain electrode 14. For example, $V_{SD}$ is between about 1 V and 2 V.

In step S304 the threshold gate voltage $V_{TH}$ is calculated. There are several ways to calculate $V_{TH}$ that would fall within the customary practice for the person skilled in the art. According to a preferred embodiment, the current $I_D$ at the drain electrode 14 of the FET is measured at increments of the gate voltage $V_G$. For example, $I_D$ is measured for values of $V_G$ between 0 V and −40 V in increments of 0.1 V. An $I_D/V_G$ curve is then plotted. The linear region of the $I_D/V_G$ curve is identified and extrapolated to the intersect with the $I_D=0$ axis such that the threshold $V_G$ at this intersect is determined. In alternative embodiments, the maximum value of the second derivative of the $I_D/V_G$ curve is calculated (i.e. $\partial^2 I_D/\partial V_G^2$) and the gate voltage value corresponding to the maximum value is determined.

The change in $V_{TH}$ (i.e. $\Delta V_{TH}$) is then calculated by subtracting the value of $V_{TH}$ measured in step S304 from the $V_{TH}$ of the FET when it is in pure air.

In step S305, the calculated change in $V_{TH}$ is compared with a threshold. According to a preferred embodiment, the comparison is performed by looking up the calculated change in $V_{TH}$ in a lookup table stored in a memory 36.

If the calculated change in $V_{TH}$ is greater than the threshold, it is determined that BTEX gas molecules are present in step S306.

In optional step S308, the type of BTEX gas molecules present are estimated based on the calculated change in $V_{TH}$, the type of arene compound used and the respective lookup table. For example, toluene molecules are shown (see FIG. 6c) to increase $V_{TH}$ minimally over the $V_{TH}$ when the gas detector 100 is in pure air for a particular calix[4]arene derivative. Therefore, if the change in $V_{TH}$ relative to the reference $V_{TH}$ is in the region of 0.25 V when that calix[4] arene derivative is used, it is likely that toluene is present in the surrounding atmosphere.

Conversely, benzene molecules have a relatively much greater effect on $V_{TH}$ (see FIG. 6c) for that same calix[4] arene derivative. If the change in $V_{TH}$ relative to the reference $V_{TH}$ is about 0.45 V, then it is likely to be the case that either low concentration benzene is present, or high concentration toluene is present (low and high concentrations being relative to BTEX gas molecules). In the event that the change in $V_{TH}$ is high when that calix[4]arene derivative is used, for example 0.7 V, then it is likely to be the case that a high concentration of benzene molecules are present in the surrounding atmosphere. Typically, detecting benzene molecules is a challenging task, and so being able to differentiate between benzene and toluene makes the gas detector 100 more effective than prior art devices.

If the change in $V_{TH}$ is not greater than a threshold value, then it is determined in step S307 that BTEX gas molecules are either not present in the surrounding atmosphere, or are present in such a low quantity so as to have insignificant effect on public health.

The gas detector 100 may be configured to alert a user to the presence of BTEX gas molecules, or concentrations of BTEX gas molecules that pose a risk. In some embodiments, as a final step after step S307 or S308, the gas detector 100 is configured to alert the user by flashing the display 34 or displaying a message on the display 34. In other embodiments, an audio alert is generated.

It would be readily appreciated by the skilled person that steps S301 and S302 are fabrication steps, and need not be carried out immediately prior to steps S303 to S308 being performed. In other words, building the gas detector 100 and using the gas detector 100 are not necessarily steps performed by the same entity.

Figure 4:
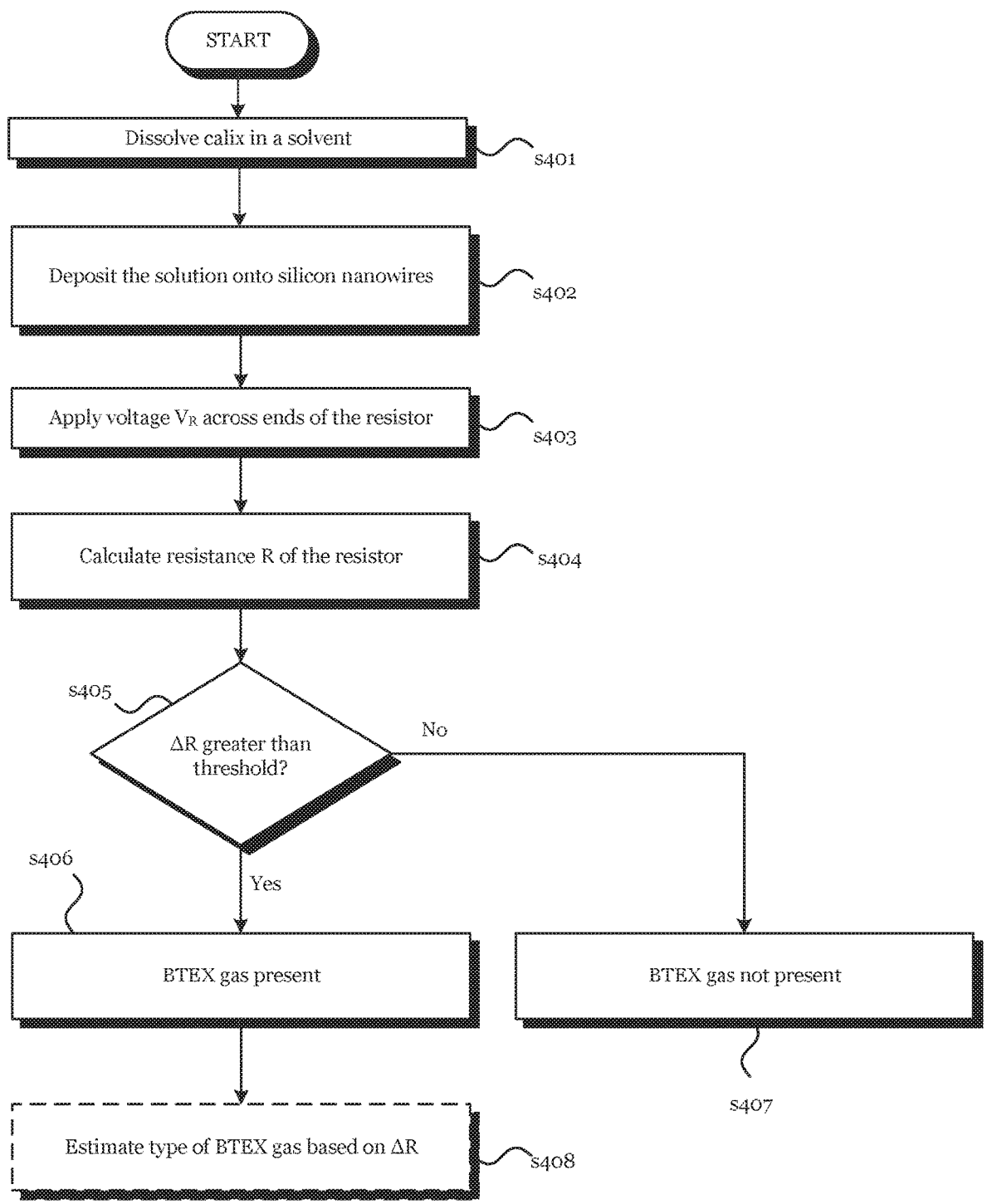
FIG. 4 is a flowchart showing a method of detecting gas according to another embodiment of the present invention.

The method described with reference to FIG. 3 uses a gas detector 100 having a transducer 10 comprising a field effect transistor (FET) whose electrical characteristics change when BTEX gas molecules are present. A method will now be described with reference to FIG. 4 where the FET is replaced by a resistor in series with the controller 32.

Steps S401 and S402 are respectively the same as steps S301 and S302, and the description of which will not be repeated. In step S403, a voltage $V_R$ is applied across ends of the resistor. For example, between 1 and 2 Volts is applied across ends of the resistor.

In step S404, the resistance R of the resistor is calculated. R is calculated by measuring the current $I_R$ across the resistor and dividing $V_R$ by $I_R$.

In step S405, the change in resistance of the resistor is calculated and compared with a threshold. In other words, the resistance measured in step S404 is subtracted from the resistance of the resistor in pure air. The threshold change in resistance indicates whether a significant enough concentration of BTEX gas molecules is present to pose a risk to health. For example, a minimal change in resistance, below the threshold, indicates that BTEX gas molecules are not present in the atmosphere in sufficient quantity to pose a danger.

The determination of whether or not BTEX gas molecules are present is then determined in steps S406 to S408. These steps are substantially the same as steps S306 to S308 and their description will not be repeated here.

Figure 6A:
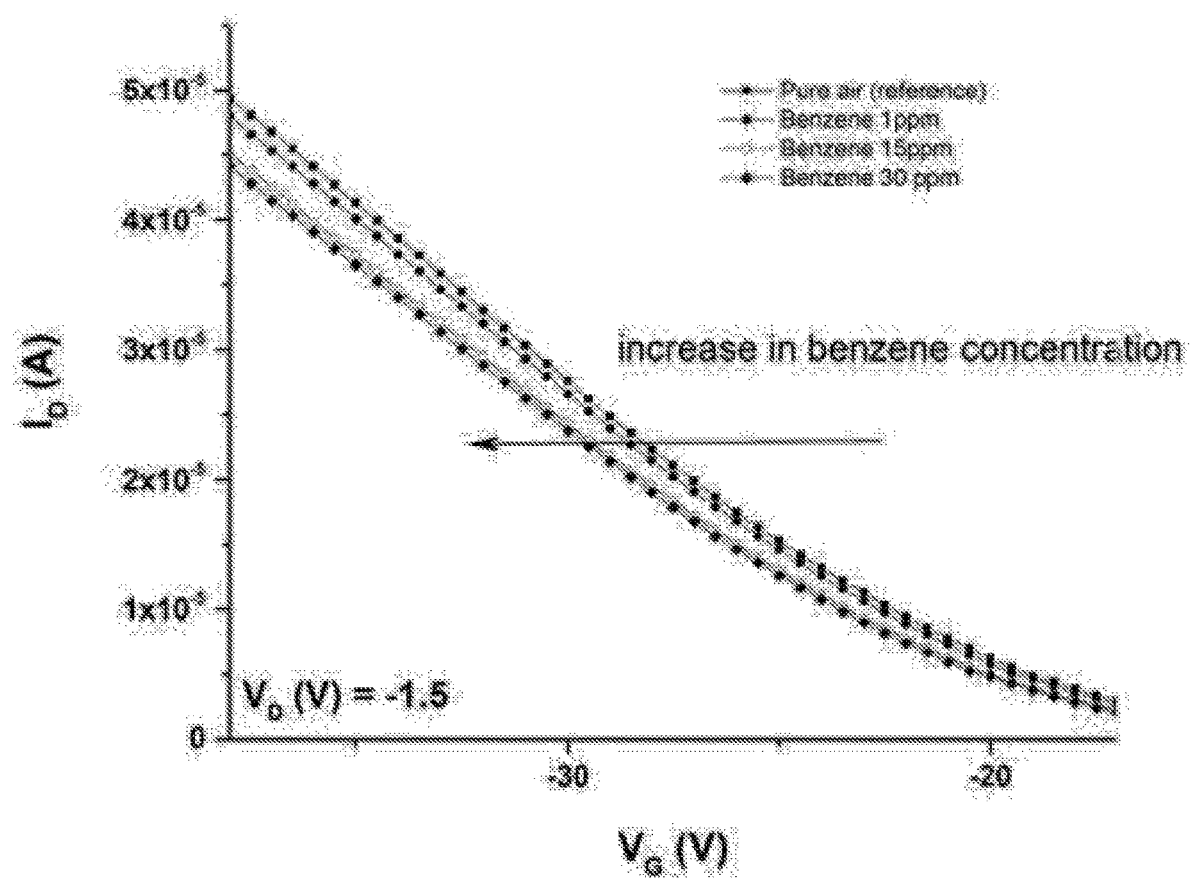
FIG. 6a is a graph of gate voltage against current for a calix[4]arene-modified silicon nanowire field effect transistor (FET) exposed to BTEX VOC vapours from 1 to 30 parts per million (ppm)

FIG. 6a shows a graph of $V_G$ against $I_D$ for a calix[4]arene-modified silicon nanowire FET exposed to BTEX VOC vapours from 1 to 30 parts per million (ppm). As the benzene concentration increases, the curves shift further to the left of the graph. In other words, when comparing a low benzene concentration (such as 1 ppm) and a high benzene concentration (such as 30 ppm), a greater current $I_D$ is able to pass across the source electrode 12 and the drain electrode 14 for the lower concentration for the same gate voltage. In other words, higher benzene concentrations increase the resistance of the nanowires 20 and effectively block current passing from the source electrode 12 to the drain electrode 14.

Figure 6B:
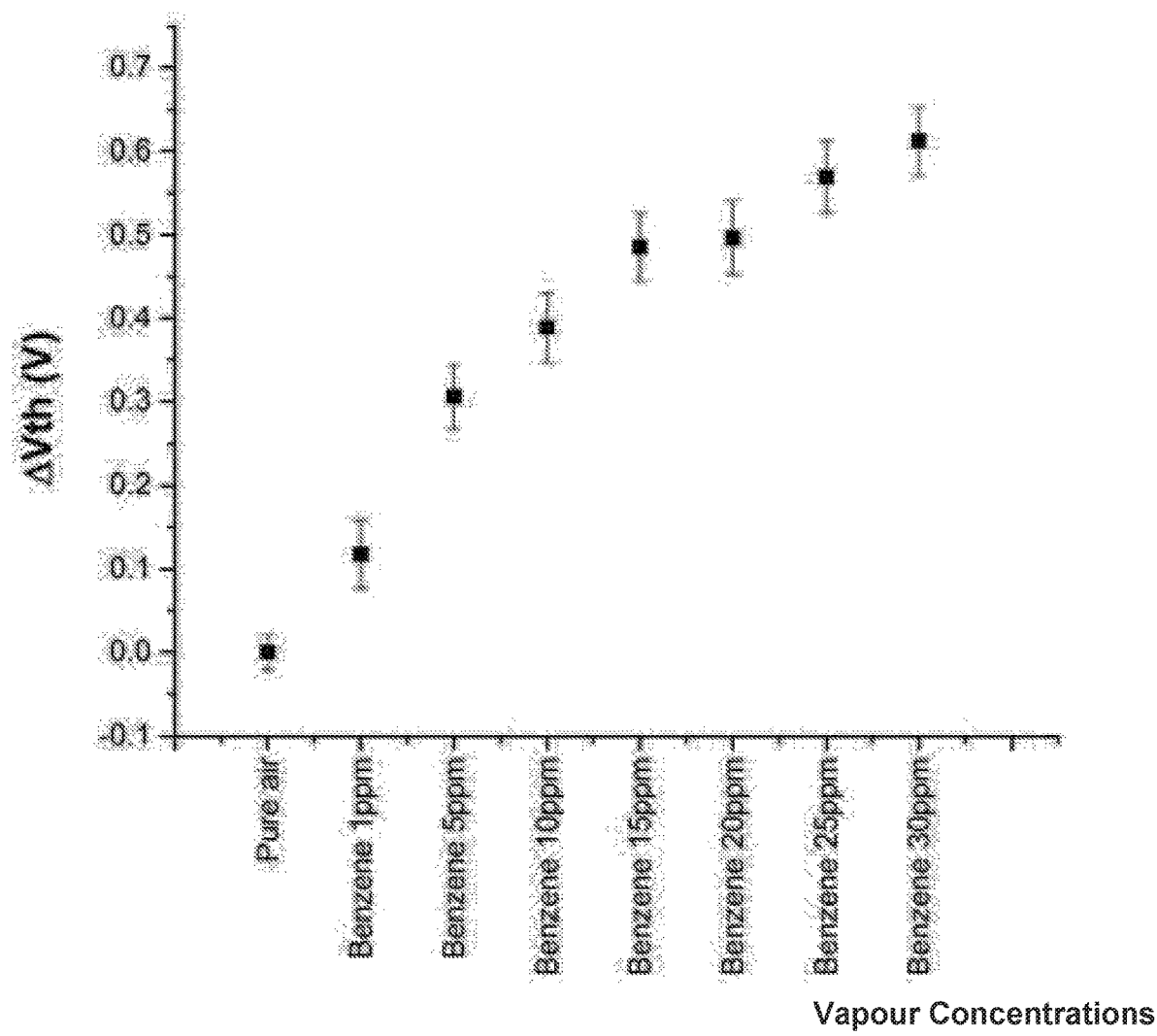
FIG. 6b is a graph of threshold voltage $V_{TH}$ measurements of a calix[4]arene-modified silicon nanowire FET exposed to BTEX VOC vapours from 1 to 30 parts per million (ppm)

Consequently, as shown in FIG. 6b, a higher gate voltage (and consequently a greater change in threshold voltage $\Delta V_{TH}$) is necessary to turn the FET on when a high concentration of benzene is present.

Figure 6C:
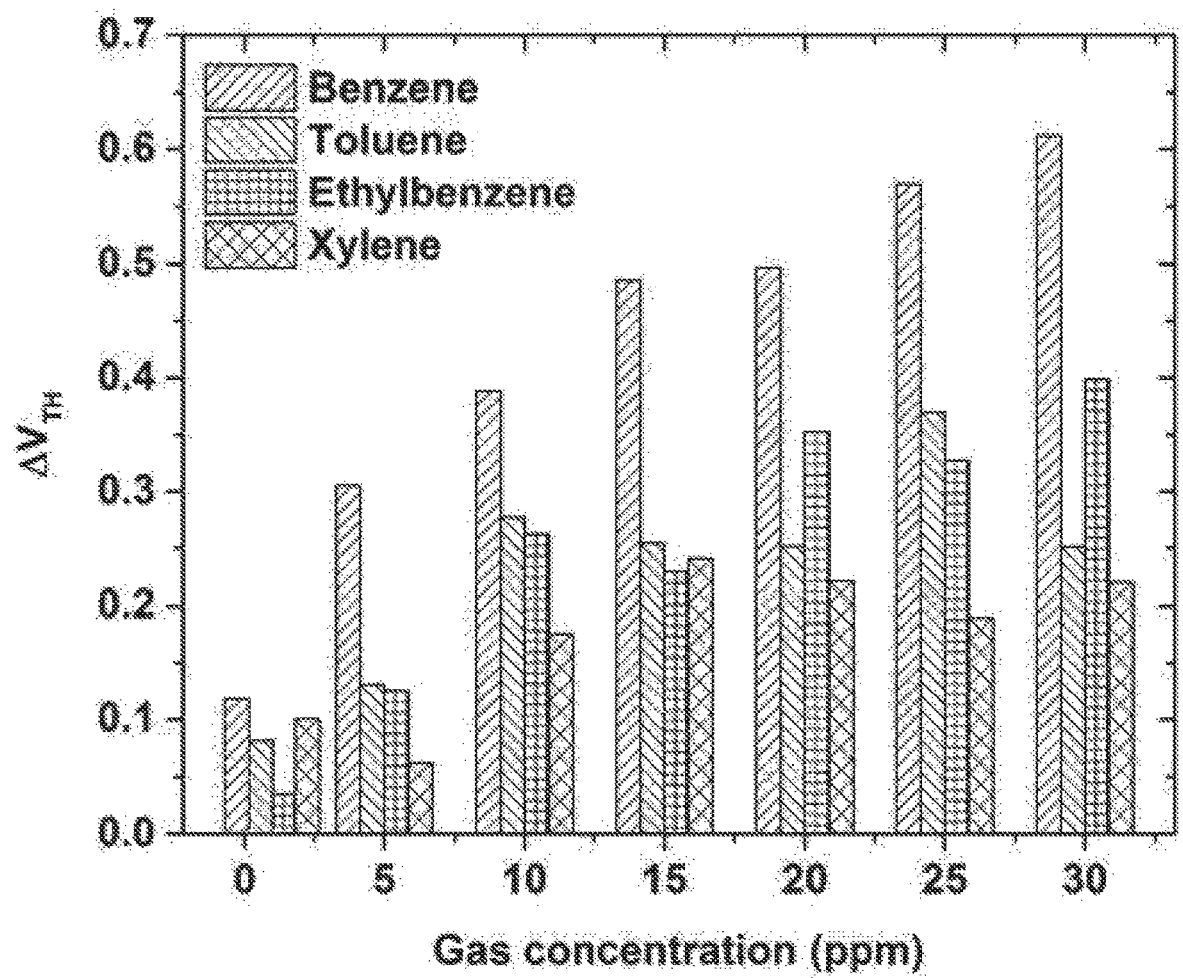
FIG. 6c is a graph of $V_{TH}$ against gas concentration for each of the BTEX VOC vapours.

FIG. 6c shows a graph of change in threshold voltage against each of the BTEX VOC gas types at different concentrations. It is clear that the gas sensor 100 is most sensitive to benzene, as this is the gas that results in the greatest change in threshold voltage $V_{TH}$.

Advantages of the gas detector 100 reside in the provision of an arene compound for capturing BTEX gas molecules. This improves the accuracy of the gas detector 100 relative to prior art detectors, and allows the gas detector 100 to differentiate between benzene and toluene. More especially, the arrangement is able to function in humid environments.

The invention claimed is:

1. A gas detector for detecting benzene, toluene, ethylbenzene or xylene (a BTEX gas), the detector comprising at least one transducer comprising:
    a field effect transistor (FET) comprising a source electrode, a gate electrode, and a drain electrode;
    at least one silicon nanowire with a native oxide shell layer, the at least one silicon nanowire extending and coupled between the source electrode and the drain electrode; and
    an arene compound, wherein the arene compound is disposed on the at least one silicon nanowire and is configured to capture a BTEX gas,
    wherein an electronic characteristic of the transducer changes when a BTEX gas is captured by the arene compound.

2. The gas detector according to claim 1, wherein the BTEX gas is benzene.

3. The gas detector according to claim 1, wherein the arene compound comprises a calixarene compound and/or wherein the arene compound is selected from a group consisting of: calix[4]arene; resorc[4]arene; pyrogallol[4]arene; and calix[5]arene.

4. The gas detector according to claim 1, wherein the gas detector comprises a power source for driving a gate voltage ($V_G$) and a source voltage ($V_{SD}$).

5. The gas detector according to claim 1, further comprising a controller configured to measure the electronic characteristic of the transducer and determine whether a BTEX gas is captured.

6. The gas detector according to claim 5, wherein the controller is configured to measure the threshold gate voltage ($V_{TH}$) necessary to drive the FET, calculate the change in $V_{TH}$ relative to a predetermined $V_{TH}$, and compare the change in $V_{TH}$ with a threshold, wherein a BTEX gas is determined to be captured if the change in $V_{TH}$ is greater than a threshold, optionally wherein the controller is configured to measure $V_{TH}$ by:
    increasing a gate voltage ($V_G$) in increments and measuring the current ($I_D$) at the drain electrode for each increment of $V_G$ to plot an $I_D/V_G$ curve;
    identifying the linear region of the $I_D/V_G$ curve; and
    extrapolating the linear region to the intersect with the $I_D=0$ axis such that the threshold $V_G$ at this intersect is determined;
or the controller is configured to measure $V_{TH}$ by:
    increasing $V_G$ in increments and measuring the current $I_D$ at the drain electrode for each increment of $V_G$ to plot an $I_D/V_G$ curve; and
    measuring $V_{TH}$ by determining the gate voltage value corresponding to the maximum value of the second derivative of the $I_D/V_G$ curve.

7. The gas detector according to claim 6, further comprising:

a storage device for storing a lookup table for comparing the change in $V_{TH}$, BTEX gas type and the concentration of the BTEX gas, optionally wherein the controller is configured to determine the BTEX gas type and the concentration of BTEX gas using the lookup table and the measured change in $V_{TH}$; and/or a plurality of transducers arranged in a matrix, each transducer comprising a different arene compound; and/or at least one of a display device and an audio device, wherein the controller is configured to alert a user to the presence of a BTEX gas if the electronic characteristic changes more than a threshold amount; and/or an interface for transmitting an indication of the presence of a BTEX gas to an external computing device.

8. A mobile device comprising the gas detector according to claim 1.

9. The mobile device according to claim 8, wherein the mobile device comprises a smart phone or a tablet.

10. A method of detecting benzene, toluene, ethylbenzene or xylene (a BTEX gas) using a gas detector comprising at least one transducer, wherein the transducer comprises a field effect transistor (FET) comprising a source electrode, a gate electrode, and a drain electrode, the method comprising:

applying a voltage across ends of at least one silicon nanowire with a native shell oxide layer, wherein the silicon nanowire is coupled and extending between the source electrode and the drain electrode and an arene compound is disposed on the at least one silicon nanowire and is configured to capture a BTEX gas, wherein an electronic characteristic of the transducer changes when the BTEX gas is captured by the arene compound; and measuring the electronic characteristic and determining whether a BTEX gas is captured by the arene compound.

11. The method according to claim 10, wherein measuring the electronic characteristic comprises:

measuring the threshold gate voltage ($V_{TH}$) necessary to drive the FET at a predetermined source voltage ($V_{SD}$);

calculating the change in $V_{TH}$ relative to a predetermined $V_{TH}$, and comparing the change in $V_{TH}$ with a threshold, wherein, a BTEX gas is determined to be captured if the change in $V_{TH}$ is greater than a threshold.

12. The method according to claim 10, comprising:

alerting a user to the presence of a BTEX gas if the electronic characteristic changes more than a threshold amount; and/or transmitting an indication of the presence of a BTEX gas to an external computing device.

13. A method of manufacturing a gas detector, comprising:

coupling at least one silicon nanowire with a native shell oxide layer between ends of a transducer, wherein the transducer comprises a field effect transistor (FET) comprising a source electrode, a gate electrode, and a drain electrode and the silicon nanowire is coupled and extends between the source electrode and the drain electrode; and applying an arene compound to the at least one silicon nanowire, wherein the arene compound is configured to capture benzene, toluene, ethylbenzene or xylene (a BTEX gas).

14. The method of manufacturing a gas detector according to claim 13, comprising:

dissolving calix in an organic solvent to produce a calixarene, wherein the arene compound comprises the calixarene;

applying the calixarene compound to the at least one silicon nanowire; and baking the transducer to evaporate the residues of the dissolving solvent.

15. The method of manufacturing a gas detector according to claim 14, comprising dissolving the calix in toluene or chloroform.

16. The method of manufacturing a gas detector according to claim 14, wherein applying the calixarene compound to the at least one silicon nanowire comprises:

spin-coating the calixarene compound, optionally wherein the calixarene compound is spin-coated at about 500-3000 rpm for at least 5 seconds; or drop-casting the calixarene compound.

* * * * *